Figure 1:
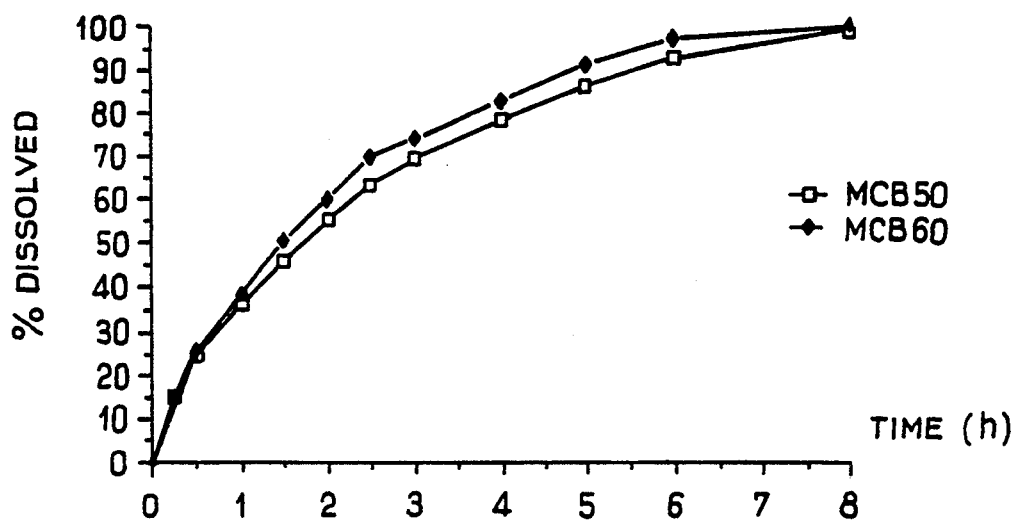

United States Patent [19]

Aiache

[11] Patent Number: 5,362,498
[45] Date of Patent: Nov. 8, 1994

[54] PROCESS FOR PREPARING A BIOADHESIVE PHARMACEUTICAL DOSAGE FORM AND PHARMACEUTICAL DOSAGE FORM THUS PREPARED

[76] Inventor: Jean-Marc Aiache, 17 rue Maréchal Galliéni, 63000 Clermond-Ferrand, France

[21] Appl. No.: 975,585
[22] PCT Filed: Jul. 30, 1991
[86] PCT No.: PCT/FR91/00630
§ 371 Date: Feb. 1, 1993
§ 102(e) Date: Feb. 1, 1993
[87] PCT Pub. No.: WO92/02209
PCT Pub. Date: Feb. 20, 1992

[30] Foreign Application Priority Data
Jul. 31, 1990 [FR] France ................. 90 09752

[51] Int. Cl.$^5$ ............... A61F 13/02; A61K 47/42
[52] U.S. Cl. ....................... 424/435; 514/773; 514/953
[58] Field of Search ............ 424/435; 514/773, 953

[56] References Cited

U.S. PATENT DOCUMENTS 3,133,862  5/1964  Wershaw et al. ............ 424/602
4,572,832  2/1986  Kigasawa et al. ........... 424/435
4,915,948  4/1990  Gallopo et al. ............. 424/435

FOREIGN PATENT DOCUMENTS 0306454  3/1989  European Pat. Off. .

OTHER PUBLICATIONS

Proceed. Intern. Symp. Control. Rel. Biact. Mater., 21 (1994), Controlled Release Society, Inc., Beysac et al, "Development and Pharmacokinetic Evaluation of S2005 Bioadhesive Buccol Tablet".

Proceed. Internal. Symp. Control. Rel. Bioact. Mater., 21 (1994), Controlled Release Society, Inc., Beyssac et al, "Development and Pharmacokinetic Evaluation of S2005 Bioadhesive Buccal Tablet".

Primary Examiner—Thurman K. Page
Assistant Examiner—C. Azpuru
Attorney, Agent, or Firm—Wegner, Cantor, Mueller & Player

[57] ABSTRACT

The present invention relates to a process for preparing a bioadhesive sustained-release pharmaceutical dosage form, characterized in that:
a) at least a part of the active principles is mixed with a quantity of natural proteins representing at least 50% by weight of active principle, and with 0.5 to 10% of a hydrophilic polymer,
b) the mixture obtained at the end of step a is subjected to granulation in the presence of approximately 60° strength alcohol, followed by drying to bring it to a moisture content of approximately 3%.
c) the granules thereby obtained, after sizing, are mixed with standard formulation excipients, especially ballast materials, lubricants, flavorings and sweeteners,
d) the mixture obtained at the end of step c, is subjected to tabletting for the purpose of obtaining bioadhesive sustained-release tablets.

It also relates to a pharmaceutical dosage form displaying long-lasting properties of adhesiveness to the mucosae.

9 Claims, 1 Drawing Sheet

PROCESS FOR PREPARING A BIOADHESIVE PHARMACEUTICAL DOSAGE FORM AND PHARMACEUTICAL DOSAGE FORM THUS PREPARED

The present invention relates to a bioadhesive pharmaceutical dosage form and to a process for preparing it. It relates, in particular, to a controlled-release pharmaceutical dosage form which can remain attached to all mucosae, buccal, perlingual, nasal, vaginal or rectal, for an extended period.

The therapeutic efficacy of a medicinal product is conditioned by its bioavailability, that is to say the proportion of active principle reaching the general circulation, and according to the relevant kinetic behavior.

One of the aims of pharmaceutical formulations is hence to obtain a dosage form that displays good bioavailability and whose administration is readily accepted by the patient.

The oral route constitutes one of the routes initially favored, on account of its ease of administration and its low cost. The medicinal products thus administered may be absorbed over the whole length of the digestive tract. As a result, they will undergo various degradations under the action of enzymes, of digestive juices and also of pH variations.

In addition, after absorption in the stomach, duodenum or intestine, the active principles will first be transported to the liver, where they may be metabolised, leading, more often than not, to an at least partial inactivation of the compounds. The kinetics of distribution are, furthermore, difficult to control.

Parenteral administration enables this hepatic first-pass effect to be avoided. A rapid but transient effect is obtained, which makes repeated injections mandatory in order to maintain an active concentration. There are hence constraints for the patient, and risks of side effects as a result of the high plasma concentrations which are rapidly attained. In the case of substances capable of giving rise to addiction, such as, for example, opiates, the risk of dependence is enhanced.

An especially advantageous route is hence the administration of products via the buccal mucosa, with a view to local absorption through the epithelium. In effect, conditions favorable to the absorption of medicinal products exist in the buccal cavity: thin, multicellular epithelium, weakly acid pH and rich vascularization permitting a rapid passage through the mucosa to the blood stream. A higher blood concentration than that obtained after absorption at a lower level from the gastrointestinal tract is often observed. This is due to the fact that the efferent blood flows via the maxillary and sublingual pathways into the external jugular vein, thereby preventing the active principle absorbed from undergoing a rapid bioconversion by the liver, as can occur with molecules absorbed in the intestine. However, in addition, the active principle escapes the action of the pH variation of the different levels of the digestive tract, and the action of enzymes and, where appropriate, a complexing with food substances. The route in question is hence one that combines the good bioavailability of the parenteral route with the ease of administration of the oral route.

Administration via the other mucosae, rectal, perlingual, nasal or vaginal, will also display good absorption characteristics by avoiding the hepatic first-pass effect. A local action, such as, for example, an antiseptic, antifungal, anti-inflammatory or astringent action, may also be sought, whence the advantage of a dosage form capable of remaining in place for an extended period.

For oral administration, lyophilized dosage forms have been used. These are, more often than not, tablets for the perlingual route, displaying a rapid disintegration on rehydration by the saliva, providing the active principle with a rapid but short-lived action.

Various problems arise for maintaining the active principle in contact with the mucosa for the longest possible time, and in order to be able to regulate the release of the active principle from this dosage form under the strictest conditions so as not to cause massive absorption and not to interfere with the patient's life by putting, in the case of forms for buccal absorption, an annoying dosage form in his or her mouth.

Many bioadhesive dosage forms have been proposed hitherto; they were all based on the use of mixtures of polymers (pectins, cellulose derivatives, polycarbophils) which are viscous polymers in solution and which display properties of adhesiveness resembling glues. The formulae produced generally display adhesiveness, but the latter lasts barely longer than one hour.

Thus, the present invention relates to a process for preparing a bioadhesive sustained-release pharmaceutical dosage form, characterized in that:

a) at least a part of the active principles is mixed with a quantity of natural proteins representing at least 50% by weight of active principle, and with 0.5 to 10% of a hydrophilic polymer, b) the mixture obtained at the end of step a is subjected to granulation in the presence of approximately 60% alcohol, followed by drying to bring it to a moisture content of approximately 3%.

c) the granules thereby obtained, after sizing, are mixed with standard formulation excipients, especially ballast materials, lubricants, flavorings and sweeteners, d) the mixture obtained at the end of step c, is subjected to tabletting for the purpose of obtaining bioadhesive sustained-release tablets.

Bioadhesive dosage form is understood to mean a dosage form displaying a capacity for adhesion to biological tissues, especially to the mucosae. The formation of bioadhesive bonds takes place between a component of the pharmaceutical dosage form, in general a polymer, and the mucus coating the membranes, when there are strong interactions between the two surfaces. The bonds in question may be physical, mechanical or chemical in nature.

In the process according to the present invention, the component that establishes bonds with the tissues consists of natural proteins which have not undergone any modification. These natural proteins do not display toxicity and their cost is low.

These proteins are defined by their functional properties, that is to say the collective non-nutritional properties that influence their usefulness, namely the physicochemical properties which make it possible to contribute to desired characteristics of the composition in which they participate. These properties stem from complex interactions between the composition, the structure, the confirmation and the physicochemical properties of the proteins among themselves and with the other components of the composition.

The functional properties are characteristic of a protein or of a mixture of proteins.

Proteins possess a macromolecular structure which characterizes them as a polymer.

The other properties enabling them to be adopted as the main excipient in the process according to the present invention are:

hydration properties: adsorption, swelling, adhesion, viscosity, properties dependent upon protein/protein interactions which occur during phenomena such as precipitation, gelation and structure formation, surface properties: they possess emulsifying and foaming properties.

An optimal expression of these properties, especially the capacity for swelling, the properties of adhesiveness and the slowness of disintegration due to structure formation, is obtained for contents of natural proteins representing at least of the order of 50% by weight of the active principle or principles used. This content may be varied according to the volume of active principle used, since proteins also play the part of a binder and diluent. An increase in the percentage of proteins enables the potential for water uptake to be enhanced. The active principle/protein ratio depends on the content of active principle in the tablet, which is itself dependent on the dose needed for obtaining pharmacological activity. This ratio can hence vary over very considerable proportions.

A small quantity of a hydrophilic polymer, of the order of 0.5 to 10%, enables these functional properties to be fortified as a result of its gelling properties. The quantity used will be dependent on the desired rate of acquisition of adhesive power. A quantity of polymer of the order of 5% will preferably be used. This polymer may be an organic polymer, for example a gum arabic, gum tragacanth, guar gum, carob, starch, alginic acid and alginates, carrageenates, agar-agar, cellulose derivatives such as methyl cellulose, ethyl hydroxyethyl cellulose, carboxymethyl cellulose, hydroxypropyl methyl cellulose, Avicel RC 581, xanthan gum or gelatin.

Depending on the type and the proportion used, the rate and intensity of bioadhesion can be varied. Furthermore, the polymer gives the proteins a better capacity for tabletting and strengthens the cohesion of the tablet by promoting hydration of the proteinaceous medium.

According to one of the preferred aspects of the present invention, hydroxypropyl methyl cellulose (or HPMC) is used.

Preferably, the quantity of natural proteins introduced in step a) represents 50 to 150% by weight of the active principles, but it is, of course, understood that a person skilled in the art can increase this percentage according to parameters which he will be in a position to determine.

A wet granulation is performed in the presence of approximately 60% alcohol. It is important that the alcohol titer should not be too high, in order to avoid denaturation of the natural proteins and to maintain their properties of bioadhesiveness. An alcohol strength much above 60% would bring about cleavage of the intramolecular bridges and modification of the electrophoretic properties, resulting in a loss of bioadhesiveness, Depending on the conditions of granulation and drying (oven or fluidized-air bed, for example), granules of different particle sizes are obtained. Oven drying at 45° C. will be preferred.

A sizing enables granules to be recovered having the appropriate diameter in accordance with the desired kinetics of subsequent release. In effect, it is found that release of the active principle is slowed down in the case of granules having an average diameter of more than 1 mm.

The standard tabletting excipients can comprise ballast materials and lubricants, such as talc, corn starch and stearates. In particular, a quantity of corn starch not exceeding 5% will reinforce the hardness of the tablet and prevent its premature disintegration. The nature of the excipient added to the proteins enables the adhesion strength to be increased. A mutual fortification of the properties of adhesiveness of the various constituents chosen from proteins, starch and cellulose, and of the gelling properties, is observed.

In the case of tablets intended for the buccal route, flavorings (for example mint essential oil in powder form) and sweeteners (such as aspartame), designed to make administration more pleasant and, where appropriate, to mask the taste of the active principles, will be added to the composition.

The granules are mixed with the excipients, in general in a Turbula ® mixer, and then subjected to tabletting in order to obtain bioadhesive tablets which will gradually release the active principle.

According to one of the aspects of the invention, the active principles are introduced in their entirety in the first step of the preparation. A latency time will then be observed before the active principles begin to be released.

According to another aspect of the invention, a residual quantity of active principle, corresponding to 5 to 10% by weight of the total amount of active principles participating in the formula, is added in non-granular form before tabletting. Once the dosage form is moistened, this fraction of active principle will be able to be released rapidly and will play the part of a primer by reducing the latency time of therapeutic activity, whereas two-layer tablets cannot be envisaged for retaining the bioadhesive properties.

The natural proteins used can be proteins extracted from soya bean.

The natural proteins used can be milk proteins, or milk protein concentrates.

The milk protein concentrates are powders obtained from pasteurized raw milk excluding any other ingredient. Depending on the techniques employed, the casein fraction, the total milk proteins or the whey proteins may be recovered. The production techniques make use either of purely physical processes, gel filtration and ultrafiltration, or of heat-coagulation processes.

Depending on the protein fraction recovered, the following are distinguished:

Casein Protein Concentrates

These are obtained by the insolubilization of casein at its isoelectric point. The coagulum obtained is then washed extensively and thereafter dried, leading to the production of a powder containing only casein as a protein component. The coagulum may also be solubilized with an alkali; after neutralization of the soluble protein concentrates, caseinates are obtained.

Concentrates of Total Milk Proteins

The total milk proteins are recovered from skimmed milk after ultrafiltration. This technique enables them to be concentrated selectively by separating them from the carbohydrates and soluble minerals of the milk. The proteins thereby collected are in the native state, without substantial modification or denaturation.

Whey Protein Concentrates

Whey or milk serum is the byproduct of the production of cheese and casein. After enzymatic coagulation for cheese making, the whey is the yellow-green liquid residue obtained by separation. It may be likened to a dilute solution of mineral salts, lactose and proteins of high nutritional quality. The concentration of whey is carried out by ultrafiltration, ion exchange chromatography or thermal precipitation.

Irrespective of the technique used, the final product is a more or less agglutinated, white to yellowish powder with a characteristic odour of milk, containing, apart from a protein fraction, lactose, fats and mineral salts in defined quantities that vary according to the type of product. Among the minerals, calcium and phosphorus are the most important in milk. During concentration by ultrafiltration, these minerals are concentrated with the proteins.

A single type of protein or a mixture may be used. The best results are obtained with concentrates of total milk proteins, which enable granulation and tabletting to be carried out without difficulty.

The use of milk proteins makes it unnecessary to add lactose before tabletting.

It is possible to use a mixture of a small percentage of whey protein concentrates with total protein concentrates.

According to one of the preferred aspects of the invention, Prosobel is used, especially Prosobel L85 ® which gives a tablet possessing a slow disintegration time (less than that obtained, for example, with Prosobel L60 ®) and substantial swelling.

Implementation of this process makes it possible to obtain a pharmaceutical dosage form displaying long-lasting properties of adhesiveness to the mucosae, characterized in that it contains, apart from the active principles, natural proteins in an amount representing at least 50% by weight of the active principles, a hydrophilic polymer, and standard excipients enabling the formulation to be stabilised.

Preferably, the content of natural proteins is between approximately 50% and 150% by weight of the active principles.

In effect, proteins, especially milk protein concentrates, form a network after wet granulation and tabletting, enabling a dosage form to be obtained, the disintegration and behavior of which are dependent on the nature and proportion of the proteins involved. In the presence of water, the proteins form a gel and gradually swell. The top layer of the tablet rapidly hydrates, and the interactions resulting therefrom form a gelled barrier that obstructs the entry of water and enables bonds to be established between the proteins and the mucosa, for example van der Waals type bonds.

This bioadhesiveness, which is instantaneous, results from hydration of the polymer causing separation of the long chains, it then being possible for the polymer molecules to pair,
with the molecules of the mucosa (glyco-proteins),
with other molecules of the polymer itself to form cohesive bonds The pharmaceutical dosage form can take the form of round tablets approximately 8 mm in diameter and 2 to 3 mm in thickness.

It can also take the form of semi-convex tablets which correspond exactly in shape to the maxillogingival sulcus or alternatively of the cavity lying under the tongue.

In effect, according to one of the aspects of the invention, this pharmaceutical dosage form is characterized in that it is capable of remaining applied to the buccal mucosa for at least 10 min and for a period which can extend to 12 hours.

For administration via the buccal mucosa, the tablet may be placed, while holding it on the end of the finger, between the lower lip and the gum, applying gentle manual force to it. After a fairly short latency time, the tablet sticks and no longer moves. It is possible to speak and even to eat without any problem.

The invention hence provides a dosage form which is easy and inexpensive to manufacture, enabling the hepatic first-pass effect to be avoided. Being a bioadhesive sustained-release dosage form, it avoids the need for repeated doses. It preserves the patient's independence and freedom of action, resulting in an obvious psychological advantage since it can be prescribed for use outside the hospital environment. Side effects are reduced.

In the case of morphinic active principles, the absorption which also takes place to a small extent in the digestive tract on account of salivary excretion produces metabolites such as morphine 6-glucuronide, which is 1.5 times as potent.

According to another aspect of the invention, the pharmaceutical dosage form is characterised in that it is capable of remaining applied to the perlingual, nasal, rectal or vaginal mucosa for a period equal to at least 10 min, and which can extend to 12 hours.

The examples which follow are designed to illustrate the invention without in any way limiting its scope.

FIG. 1 shows the kinetics of the percentages dissolved using the paddle method, for tablets containing 50 mg (MCB50) and 60 mg (MCB60) doses of morphine sulfate.

EXAMPLE 1

Preparation of Muco-Adhesive Tablets Containing 50 mg Doses of Morphine

| Morphine (50 mg) | | |
| --- | --- | --- |
| Active principle: morphine sulfate | 50.00 mg | 38.46% |
| Prosobel L85 ® | 55.00 mg | 42.30% |
| HPMC 15,000 | 6.50 mg | 5.00% |
| Corn starch | 6.50 mg | 5.00% |
| Flavoring, mint essential oil in powder form | 5.00 mg | 3.84% |
| Aspartame | 5.00 mg | 3.84% |
| Talc | 1.00 mg | 0.76% |
| Magnesium stearate | 1.00 mg | 0.76% |
| | 130.00 mg | |

The excipients comprising the proteins participating in the composition in their entirety plus half the percentage of the flavoring and of the sweetener are sieved through a 0.8 nun sieve. They are then mixed with the active principle using a Turbula ® mixer for 10 minutes. The mixture is subjected to wetting using a planetary mixer, with a 60% alcohol solution. Granulation is then performed on an oscillating granulator having a 1.6 mm screen. The granule obtained is dried in an oven at 45° C. for 8 hours, so as to obtain a moisture content of approximately 3%. After sizing on a 1 mm screen, the granule obtained is mixed with the lubricants and the reminder of the flavoring and the sweetener, for 10 minutes using the turbula [sic]. Tabletting is carried out on a Frogerais type rotary machine with punches 8 mm in diameter. The thickness of the tablets is 2 mm.

PROSOBEL L85 ® is a total milk protein concentrate, prepared from pasteurized skimmed milk and obtainable from Fromagerie Bel, 8 rue de Penthiever, 75008 PARIS. The milk is submitted to ultrafiltration to retain high molecular weight products and eliminate lactose and mineral salts. This leads to a product of high purity and high content in proteins. The composition of PROSOBEL L85 ® is given the following table:

| | |
|---|---|
| Humidity | 3.5% |
| Proteins | 85.5% |
| Lactose | 2.0% |
| Fat | 1.5% |
| Ashes | 7.5% |

EXAMPLE 2

Preparation of Morphine Tablets Containing 60 mg Doses

| Morphine (60 mg) | | |
|---|---|---|
| Active principle: morphine sulfate | 60.00 mg | 42.85% |
| Prosobel L85 ® | 55.00 mg | 39.28% |
| HPMC 15,000 | 6.50 mg | 4.61% |
| Corn starch | 6.50 mg | 4.61% |
| Aspartame | 5.00 mg | 3.57% |
| Flavoring, mint essential oil in powder form | 5.00 mg | 3.57% |
| Talc | 1.00 mg | 0.71% |
| Magnesium stearate | 1.00 mg | 0.71% |
| | 140.00 mg | |

The tablets are prepared according to a protocol similar to that of Example 1.

EXAMPLE 3

| Buprenorphine | | |
|---|---|---|
| Buprenorphine | 0.30 mg | 0.21% |
| Lactose Codex | 39.70 mg | 28.36% |
| HPMC 15,000 | 13.00 mg | 9.29% |
| Corn starch | 13.00 mg | 9.29% |
| Prosobel L85 ® | 62.00 mg | 44.29% |
| Flavoring, mint essential oil in powder form | 5.00 mg | 3.57% |
| Aspartame | 5.00 mg | 3.57% |
| Talc | 1.00 mg | 0.71% |
| Magnesium stearate | 1.00 mg | 0.71% |
| | 140.00 mg | |

The tablets are prepared according to a protocol similar to that of Example 1.

EXAMPLE 4

Preparation of Tablets With an Anti-Spasmodic Active Principle

| Phloroglucinol | | |
|---|---|---|
| Active principle: phloroglucinol | 80.00 mg | 50.00% |
| HPMC 15,000 | 6.50 mg | 4.10% |
| Corn starch | 6.50 mg | 4.10% |
| Prosobel L85s | 55.00 mg | 34.37% |
| Flavoring, mint essential oil in powder form | 5.00 mg | 3.12% |
| Aspartame | 5.00 mg | 3.12% |
| Magnesium stearate | 1.00 mg | 0.62% |
| Talc | 1.00 mg | 0.62% |
| | 160.00 mg | |

The tablets are prepared according to a protocol similar to that of Example 1.

EXAMPLE 5

Preparation of Tablets Containing an Antiasthmatic Active Principle

| Salbutamol, 4 mg | | |
|---|---|---|
| Active principle: salbutamol sulfate | 4.00 mg | 2.86% |
| Lactose Codex | 56.00 mg | 40.00% |
| HPMC 15,000 | 6.50 mg | 4.64% |
| Corn starch | 6.50 mg | 4.64% |
| Prosobel L85 ® | 55.00 mg | 39.28% |
| Flavoring, mint essential oil in powder form | 5.00 mg | 3.57% |
| Aspartame | 5.00 mg | 3.57% |
| Talc | 1.00 mg | 0.71% |
| Magnesium stearate | 1.00 mg | 0.71% |
| | 140.00 mg | |

| Salbutamol, 8 mg | | |
|---|---|---|
| Active principle: salbutamol sulfate | 8.00 mg | 9.09% |
| HPMC 15,000 | 6.50 mg | 7.38% |
| Corn starch | 6.50 mg | 7.38% |
| Prosobel L85 ® | 55.00 mg | 62.50% |
| Flavoring, mint essential oil in powder form | 5.00 mg | 5.68% |
| Aspartame | 5.00 mg | 5.68% |
| Talc | 1.00 mg | 1.13% |
| Magnesium stearate | 1.00 mg | 1.13% |
| | 88.00 mg | |

The tablets are prepared according to a protocol similar to that of Example 1.

EXAMPLE 6

Release of the Active Principle in Vitro

The tablets obtained possess an average weight of 0.132 g, a hardness in the region of 0.61 newton and a disintegration time of more than 4 hours. The kinetics of the percentages dissolved for tablets containing 50 and 60 mg doses, respectively, of morphine are shown in FIG. 1. These kinetic measurements are carried out on a rotating paddle dissolution apparatus (Pharmacopoeia type) at a pH of 4.5 and at 60 rpm. After HPLC assay of the samples, it is found that the percentage dissolved at the end of 8 hours is 100% in both cases.

EXAMPLE 7

Results of Clinical Trials and Pharmacokinetics

These trials were carried out using tablets prepared according to Example 1.

* Clinical studies

Preliminary clinical trials were carried out on postoperative patients, and covered questioning of the patient, the activity, speed and duration of action and lastly the acceptability of the dosage form.

These studies showed that the dosage form was well accepted, since the taste was rated pleasant, surprising and novel compared to traditional medicinal products.

Analgesia began approximately ¼ hour after taking the medicinal product and lasted 8 hours. This dosage form appeared to be well tolerated by the patients, and no severe side effect was observable.

* Pharmacokinetic studies

These were carried out on patients and gave the plasma levels which follow. A visual pain scale established by the patients shows that the analgesia can last up to 18 h after taking the medicinal product.
Plasma levels

| Subject No. | Dose administered | Tmax (h) | Cmax (ng/ml) |
|---|---|---|---|
| 1 | 50 mg | 4 | 24.10 |
| 2 | 50 mg | 3.75 | 11.31 |
| 3 | 50 mg | 2 | 34.97 |
| 4 | 50 mg | 4 | 27.9 |
| 5 | 30 mg | 2.66 | 9.10 |
| 6 | 50 mg | 4 | 20.00 |
| 7 | 2 × 30 mg | 4 | 20.04 |
| 8 | 30 mg | 4 | 4.45 |
| 9 | 30 mg | 4 | 8.21 |
| 10 | 50 mg | 2 | 5.39 |

No severe side effect was observable.

I claim:

1. Process for preparing a bioadhesive sustained-release pharmaceutical dosage form, comprising:
   a) mixing at least a part of the active principles with a quantity of natural proteins representing at least 50% by weight of active principle, and with 0.5 to 10% of a hydrophilic polymer,
   b) the mixture obtained at the end of step a is subjected to granulation in the presence of approximately 60% alcohol, followed by drying to bring it to a moisture content of approximately 3%.
   c) the granules thereby obtained, after sizing, are mixed with standard formulation excipients, especially ballast materials, lubricants, flavorings and sweeteners,
   d) the mixture obtained at the end of step c, is subjected to tabletting for the purpose of obtaining bioadhesive sustained-release tablets.

2. Process for preparing a pharmaceutical dosage form according to claim 1, characterized in that the active principles are mixed in their entirety in step a.

3. Process for preparing a pharmaceutical dosage form according to claim 1, characterized in that a residual quantity of active principle, corresponding to 5 to 10% of the total weight of active principle, is mixed in nongranular form during step c.

4. Process for preparing a pharmaceutical dosage form according to claim 1, characterized in that the quantity of natural proteins mixed in step a) represents 50 to 150% by weight of the active principle.

5. Process for preparing a pharmaceutical dosage form according to claim 1, characterized in that the ballast materials comprise corn starch.

6. Process for preparing a pharmaceutical dosage forth according to claim 1, characterized in that the hydrophilic polymer is an organic polymer derived from cellulose, especially hydroxypropyl methyl cellulose.

7. Process for preparing a pharmaceutical dosage form according to claim 1, characterized in that the natural proteins are soya bean proteins.

8. Process for preparing a pharmaceutical dosage forms according to claim 1, characterized in that the natural proteins are milk proteins.

9. Process for preparing a pharmaceutical dosage form according to claim 8, characterized in that the natural proteins are concentrated milk proteins.

* * * * *